(12) United States Patent
Nelson

(10) Patent No.: US 6,439,766 B1
(45) Date of Patent: Aug. 27, 2002

(54) DIAMOND DETECTING APPARATUS AND METHOD

(76) Inventor: Oris L. Nelson, 1106 N. G St. Suite C, Lake Worth, FL (US) 33460

(*) Notice: Subject to any disclaimer, the term of this patent is extended or adjusted under 35 U.S.C. 154(b) by 0 days.

(21) Appl. No.: 09/776,876

(22) Filed: Feb. 6, 2001

(51) Int. Cl.$^7$ .................. G01N 25/18; G01N 25/72; G01R 27/08
(52) U.S. Cl. .................. 374/44; 374/374; 374/5; 324/693; 324/717
(58) Field of Search .................. 374/44, 43, 5, 374/4, 142, 45; 340/540; 324/71.1, 73.1, 149, 691, 693, 713, 717, 722, 715, 696, 703

(56) References Cited

U.S. PATENT DOCUMENTS

| | | | | |
|---|---|---|---|---|
| 4,255,962 A | | 3/1981 | Ashman | 374/10 |
| 4,324,129 A | * | 4/1982 | Goldsmid | 374/11 |
| 4,344,315 A | * | 8/1982 | Moxon et al. | 374/44 |
| 4,364,677 A | * | 12/1982 | Ashman | 374/44 |
| 4,445,367 A | * | 5/1984 | Goldsmid | 374/45 |
| 4,488,821 A | | 12/1984 | Wenckus | 374/44 |
| 4,616,939 A | | 10/1986 | Gitlis | 374/44 |
| 5,379,102 A | * | 1/1995 | Takeuchi | 356/30 |
| 6,043,742 A | | 3/2000 | Austin | 340/540 |
| 6,095,680 A | * | 8/2000 | Baratta | 374/43 |
| 6,265,884 B1 | * | 7/2001 | Menashi et al. | 324/717 |

* cited by examiner

Primary Examiner—Diego Gutierrez
Assistant Examiner—Stanley J. Pruchnic, Jr.
(74) Attorney, Agent, or Firm—Alvin S. Blum

(57) ABSTRACT

An apparatus and method for determining if a stone mounted in an electrically conductive mounting is a true diamond employs a housing to be held in one hand of a user while the other hand holds the mounting. An electrically and thermally conductive probe extends from the housing. The probe is held against the surface of the stone. Two assemblies connected to the probe measure sequentially to determine the thermal conductivity of the stone and the electrical conductivity of the stone. Displays indicate if the assemblies detect the high thermal conductivity of the stone consistent with diamond and the low electrical conductivity of the stone consistent with diamond. This apparatus distinguishes true diamond over such imitations as cubic zirconia with a lower thermal conductivity and moissanite with a higher electrical conductivity.

8 Claims, 2 Drawing Sheets

DIAMOND DETECTING APPARATUS AND METHOD

BACKGROUND OF THE INVENTION

This invention relates to apparatus for inspection of gems, and more specifically to apparatus for distinguishing a true diamond from simulated diamonds including moissanite.

DESCRIPTION OF THE PRIOR ART

The jewelry industry is often confronted with simulated diamonds of little value that are being offered as true diamonds of great value. Methods to differentiate the two have used measurement of thermal conductivity as disclosed in U.S. Pat. No. 4,255,962 issued Mar. 17, 1981 to Ashman; U.S. Pat. No. 4,616,939 issued Oct. 14, 1986 to Gitlis; and U.S. Pat. No. 4,488,821 issued Dec. 18, 1984 to Wenckus. These are based on the fact that most simulated diamonds have a much lower thermal conductivity than true diamond. There is a simulated diamond currently marketed that has a thermal conductivity so close to true diamond that it cannot be detected by these devices. This material is moissanite, a form of silicon carbide with physical properties very close to true diamond. As discussed in U.S. Pat. No. 6,043,742 issued Mar. 28, 2000 to Austin, moissanite has been distinguished in the past by measurement of electrical conductivity. Moissanite conducts electricity much more than true diamond, which is an excellent electrical insulator. Austin teaches a device that applies an alternating current to the stone, and indicates by an audible signal if the conductivity is so great as to eliminate diamond. Absence of a signal indicates that the item is a true diamond. However, if the item is a good insulator but not a diamond, his device will not sound, thereby falsely indicating that it is a true diamond. This may occur with a glass specimen, from an insulating coating, poor contact to the item, or other conditions.

SUMMARY OF THE INVENTION

It is accordingly an object of the invention to provide an apparatus and method that will differentiate between true diamond and moissanite as well as other simulated diamonds. It is another object that this be achieved with a single, hand-held instrument that is easy to operate without special skills. The apparatus of the invention is a hand-held device having a probe with a small contact at one end for contacting the surface of the gem to be tested. While the probe is contacting the gem, a first measurement is made of thermal conductivity, emitting an audible signal if the item has the high thermal conductivity of diamond, followed by a measurement of electrical conductivity. If the tests reveal that the item has the high thermal conductivity and the very low electrical conductivity of true diamond, the audible signal continues, indicating that the item is a true diamond, if, however, a high electrical conductivity is detected, a different audible signal is then emitted to indicate that it is moissanite. In addition, a red LED is lit if it is moissanite, and a green LED is lit if it is a true diamond. There is no danger in falsely indicating a true diamond because of poor contact of the probe. Indeed, the operator may try repositioning the probe if no signal is given.

These and other objects, features, and advantages of the invention will become more apparent when the detailed description is studied in conjunction with the drawings in which like elements are designated by like reference characters in the various drawing figures.

DETAILED DESCRIPTION OF PREFERRED EMBODIMENTS

Figure 1:
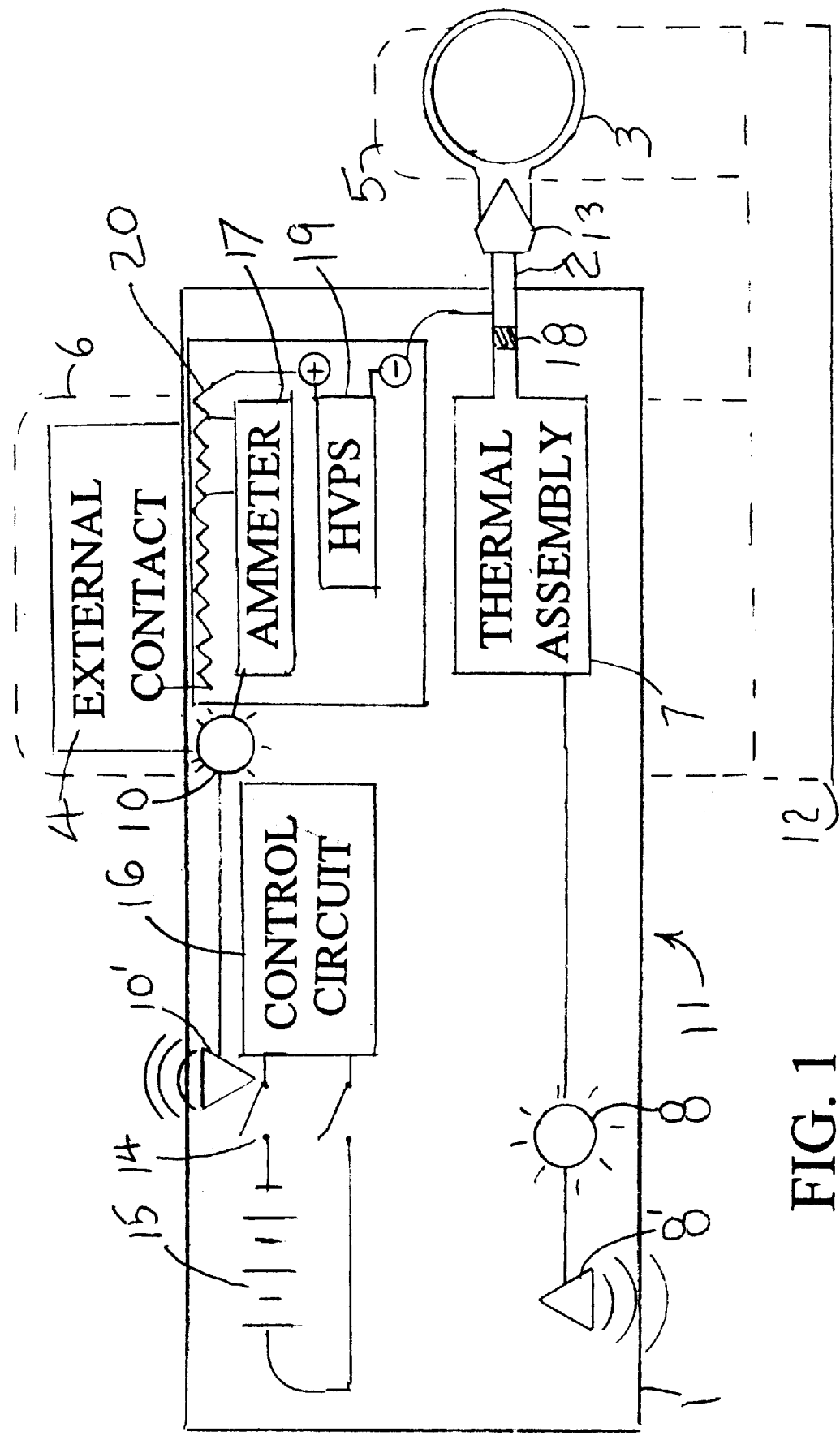
FIG. 1 is a diagrammatic view of the apparatus in use.

Referring now to FIG. 1, the apparatus 11 of the invention comprises a housing 1 that is held in (shown in phantom) a first hand 6 of a user 12 while the other hand 5 holds an electrically conductive, generally metal, mounting 3 that holds the stone 13 to be tested. An electrically and thermally conductive probe 2 extends from the housing and is applied to the surface of the stone 13. A thermal conductivity measurement assembly 7 is connected to the probe. The assembly 7 may be a type well known in the art such as that disclosed by Ashman in U.S. Pat. No. 4,255,962, for example. It indicates by displays LED 8 and buzzer 8' when the thermal conductivity is consistent with that of diamond. This eliminates most false diamonds, which have a low thermal conductivity. An on/off switch 14 and battery 15 activates control circuit 16, which indicates after a ten second warm up time that the apparatus is ready and activates the thermal assembly 7.

After a preset time, the assembly 7 is deactivated, and electrical conductivity assembly 9 is activated by control 16. Assembly 9 is connected to probe 2 and applies a positive direct current voltage of 1000 volts to external contact 4 on the housing surface that is adapted to be contacted by the second hand 6 of the user. This provides a current through the user, to the hand 5, and through the mounting 3, the stone 13, the probe 2, and back to the electrical conductivity measurement assembly 9. There, the magnitude of the current flowing is determined by current meter 17. Assembly 9 then indicates by displays LED 10 and buzzer 10' when the current and, therefor, electrical conductivity is low enough to be consistent with the low conductivity of diamond. A thermally conductive and electrically insulating spacer 18 of a material such as beryllium oxide may be provided between the thermal sensing element and the high voltage input to the probe. This effectively isolates the thermal sensor from the high DC voltage.

For measuring the very small DC current at the housing, any electrical noise signals picked up by the body are effectively reduced or eliminated by applying the positive voltage from the high voltage power supply 19 to the external contact 4 through a resistor string 20. The voltage drop across a portion of that string is measured by the DC current meter 17.

Alternatively, the displays may be so arranged that the thermal conductivity buzzer continues to sound when the electrical conductivity is being measured as low and a green LED is lit, and if the electrical conductivity measurement is high, a different sound is emitted and a red LED is lit to indicate a simulated diamond.

Figure 2:
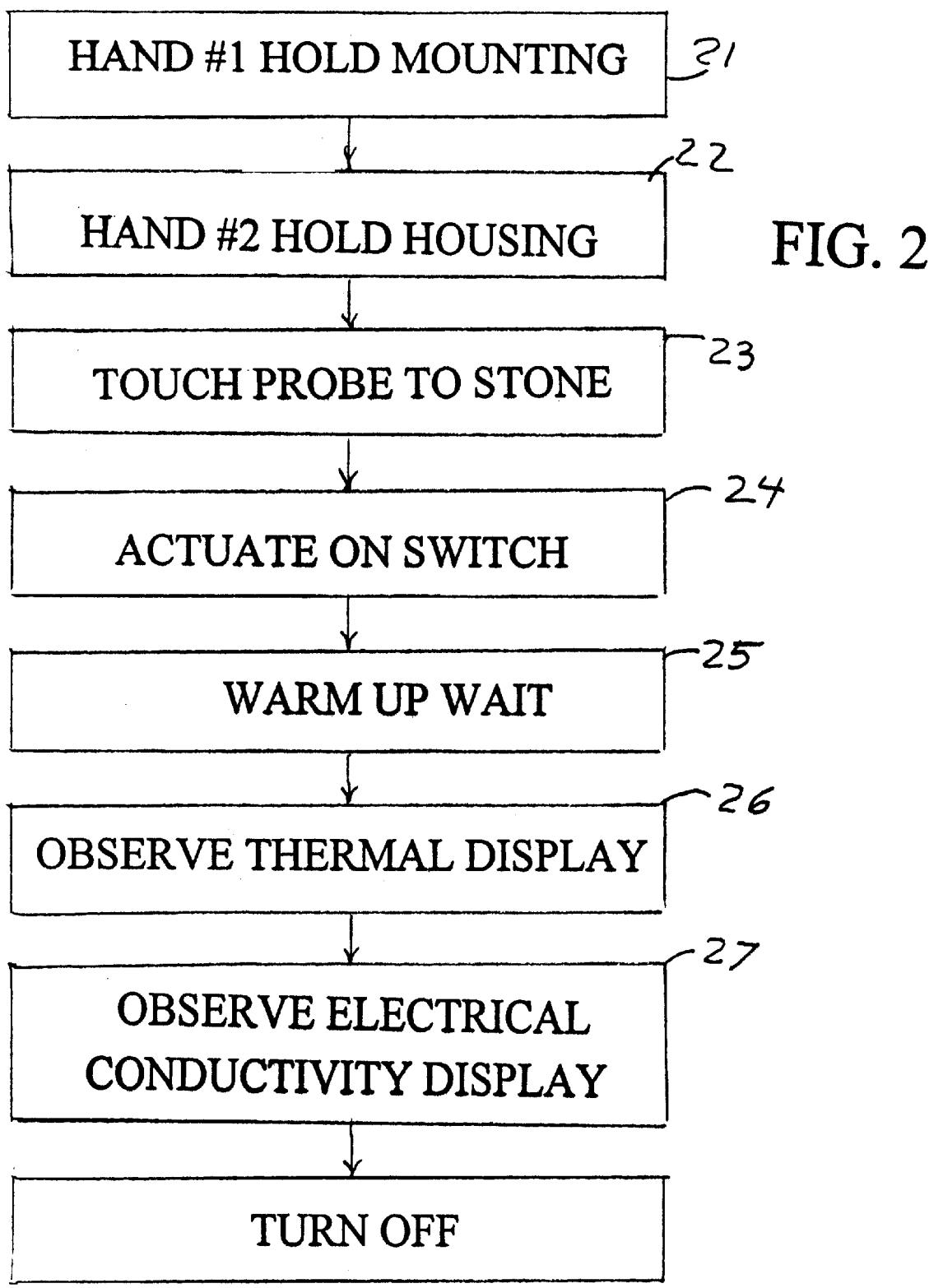
FIG. 2 is block diagram of the method of the invention.

Referring now to the method of operation, the steps of the method are depicted in FIG. 2 as follows;

The mounting of the stone is held in one hand. 22 The housing is held in the other hand. 23 The probe is applied to the surface of the stone to be tested. 24 The apparatus is turned on. 25 After a preset warm up period of about 10 seconds, 26 the thermal conductivity is measured and the results displayed. After a 0.5 second delay, 27 the electrical conductivity is measured and the results are displayed. When both the thermal and electrical conductivity displays are positive, the stone is thereby determined to be a true diamond. Furthermore, if the thermal conductivity test is positive and the electrical conductivity test is negative, it indicates that the stone is moissanite. Such simulated stones as cubic zirconia have much lower thermal conductivity than diamond.

While I have shown and described the preferred embodiments of my invention, it will be understood that the invention may be embodied otherwise than as herein specifically illustrated or described, and that certain changes in form and arrangement of parts and the specific manner of practicing the invention may be made within the underlying idea or principles of the invention.

What is claimed is:

1. Apparatus for testing a stone mounted in an electrically conductive mounting for genuineness as a diamond with a single probe applied to the stone surface, the apparatus comprising:
   a) a thermally and electrically conductive probe tip mounted in a housing;
   b) a thermal conductivity measuring assembly mounted in the housing and connected to the probe tip;
   c) an electrical conductivity measuring assembly mounted in the housing and connected to the probe tip;
   d) circuitry means in the housing connected to the two assemblies for sequentially actuating first one of the assemblies and then the other of the assemblies;
   e) thermal conductivity display means mounted in the housing and connected to the thermal conductivity measuring assembly for displaying an indication of the thermal conductivity of the stone relative to the thermal conductivity of diamond; and
   f) electrical conductivity display means mounted in the housing and connected to the electrical conductivity measuring assembly for displaying an indication of the electrical conductivity of the stone relative to the electrical conductivity of diamond.

2. The apparatus of claim 1 further comprising:
   a) an external electrical contact on the housing surface connected to the electrical conductivity measuring assembly for completing an electrical circuit through the user when the user holds an electrically conductive item on which the stone is mounted and also holds the housing, while contacting the external electrical contact; and
   b) the electrical conductivity measuring assembly applying a high direct current voltage to the stone and measuring the direct current flowing through the stone.

3. The apparatus according to claim 2, in which the thermal and electrical conductivity display means include visible and audible displays.

4. The apparatus according to claim 3, in which the thermal conductivity measuring assembly is actuated first, and then the electrical conductivity measuring assembly is actuated to thereby indicate first if the stone has the thermal conductivity consistent with diamond, and then if the stone has the electrical conductivity consistent with diamond.

5. The apparatus according to claim 2 in which a positive direct current voltage of at least nine hundred and fifty volts is applied to the external electrical contact during the electrical conductivity measurement through a resistor string, and the current is measured by the voltage across a portion of the string.

6. The apparatus according to claim 2, in which a thermally conductive and electrically insulating spacer is interposed between the thermal conductivity measuring assembly and the probe tip.

7. Apparatus for testing a stone for genuineness as a diamond with a single probe applied to the stone surface, the apparatus comprising:
   a) a thermally and electrically conductive probe tip mounted in a housing;
   b) a thermal conductivity measuring assembly mounted in the housing and connected to the probe tip;
   c) an electrical conductivity measuring assembly mounted in the housing and connected to the probe tip for applying a high direct current voltage through the stone and measuring the direct current flowing therethrough;
   d) thermal conductivity display means mounted in the housing and connected to the thermal conductivity measuring assembly for displaying an indication of the thermal conductivity of the stone relative to the thermal conductivity of diamond;
   e) electrical conductivity display means mounted in the housing and connected to the electrical conductivity measuring assembly for displaying an indication of the electrical conductivity of the stone relative to the electrical conductivity of diamond;
   f) an external electrical contact on the housing surface connected to the electrical conductivity measuring assembly for completing an electrical circuit through the user when the user holds an electrically conductive item on which the stone is mounted and also holds the housing, while contacting the electrical contact;
   g) circuitry means in the housing connected to the two assemblies for sequentially actuating first one of the assemblies and then the other of the assemblies;
   h) the thermal and electrical conductivity display means including visible and audible displays; and
   i) in which the thermal conductivity measuring assembly is actuated first, and then the electrical conductivity measuring assembly is actuated to thereby indicate first if the stone has the thermal conductivity consistent with diamond and then if the stone has the electrical conductivity consistent with diamond.

8. A method of distinguishing between a true diamond and another stone when the stone is mounted on an electrically conductive mounting using two hands of a user the method comprising:
   a) providing a housing with a thermally and electrically conductive probe tip having both thermal and electrical conductivity measuring assemblies connected thereto, an external electrical contact connected to the electrical conductivity measuring assembly, and display means for indicating when the stone has the thermal and electrical conductivity consistent with diamond;
   b) holding the stone mounting in one hand;
   c) holding the housing in the other hand while contacting the external contact;
   d) applying the probe tip to the surface of the stone;
   e) causing the thermal conductivity measuring assembly to be actuated to thereby indicate by the display means what the thermal conductivity of the stone is relative to diamond; and
   f) causing the electrical conductivity measuring assembly to be actuated to indicate by the display means what the electrical conductivity is relative to diamond.

* * * * *